(12) United States Patent
Caparso et al.

(10) Patent No.: US 7,584,004 B2
(45) Date of Patent: Sep. 1, 2009

(54) VASCULARLY STABILIZED PERIPHERAL NERVE CUFF ASSEMBLY

(75) Inventors: Anthony Caparso, St. Louis Park, MN (US); Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 335 days.

(21) Appl. No.: 11/151,103

(22) Filed: Jun. 13, 2005

(65) Prior Publication Data
US 2006/0282145 A1 Dec. 14, 2006

(51) Int. Cl.
*A61N 1/05* (2006.01)
*A61N 1/18* (2006.01)
(52) U.S. Cl. .................. 607/118; 607/149; 600/381; 600/485
(58) Field of Classification Search ............ 607/118, 607/149; 600/381, 485
See application file for complete search history.

(56) References Cited

U.S. PATENT DOCUMENTS

| | | | |
|---|---|---|---|
| 5,215,089 A * | 6/1993 | Baker, Jr. | |
| 5,344,438 A * | 9/1994 | Testerman et al. | |
| 5,487,756 A * | 1/1996 | Kallesoe et al. | 607/118 |
| 5,634,462 A * | 6/1997 | Tyler et al. | 600/377 |
| 5,938,596 A * | 8/1999 | Woloszko et al. | 600/377 |
| 6,456,866 B1 * | 9/2002 | Tyler et al. | |
| 6,542,774 B2 * | 4/2003 | Hill et al. | 607/9 |
| 6,600,956 B2 * | 7/2003 | Maschino et al. | 607/118 |
| 6,978,174 B2 * | 12/2005 | Gelfand et al. | 607/3 |
| 2003/0216792 A1 * | 11/2003 | Levin et al. | |
| 2004/0010303 A1 * | 1/2004 | Bolea | |
| 2005/0075701 A1 * | 4/2005 | Shafer | 607/72 |

FOREIGN PATENT DOCUMENTS

| | | | |
|---|---|---|---|
| DE | 4433111 | * | 3/1996 |
| WO | WO-2006138068 A2 | * | 12/2006 |

OTHER PUBLICATIONS

"International Search Report and Written Opinion for Application No. PCT/US2006/021322, Date Mailed Nov. 21, 2007", 6 Pages.*
Sweeney, J. D., et al., "Neuromuscular stimulation selectivity of multiple-contact nerve cuff electrode arrays", *Med Biol Eng Comput.*, 33(*3 Spec No*), (May 1995), 418-25.*

* cited by examiner

*Primary Examiner*—Carl H Layno
*Assistant Examiner*—Natasha N Patel
(74) *Attorney, Agent, or Firm*—Schwegman, Lundberg & Woessner, P.A.

(57) ABSTRACT

A vascularly stabilized peripheral nerve cuff assembly is provided. One aspect of this disclosure relates to an electrode assembly used in the delivery of neural stimulation therapy. The electrode assembly includes a body adapted to at least partially encompass a blood vessel and a nerve proximate to the blood vessel. The electrode assembly also includes at least one electrode along at least a portion of the body. The at least one electrode is adapted to be electrically connected to a neural stimulator. According to an embodiment, the electrode assembly includes a spacer within the body, the spacer having a first and second end, the first end secured to an inside surface of the body and the second end adapted to pass between the vessel and the nerve and to be secured to the inside surface of the body. Other aspects and embodiments are provided herein.

40 Claims, 14 Drawing Sheets

SECTION E-E

SECTION F-F

VASCULARLY STABILIZED PERIPHERAL NERVE CUFF ASSEMBLY

TECHNICAL FIELD

This disclosure relates generally to implantable medical devices and, more particularly, to systems for providing neural stimulation therapy.

BACKGROUND

Neural stimulation has been the subject of a number of studies and has been proposed for several therapies. The autonomic system controls physiological activities of the body and the imbalance of autonomic tone is related to many diseases and conditions. Reduced autonomic balance (increase in sympathetic and decrease in parasympathetic cardiac tone) during heart failure has been shown to be associated with left ventricular dysfunction and increased mortality. Sympathetic inhibition, as well as parasympathetic activation, have been associated with reduced arrhythmia vulnerability following a myocardial infarction. Vagus nerve stimulation has been proposed to treat breathing disorders, gastrointestinal motility, eating disorders, obesity, anorexia, gastrointestinal tract disorders, hypertension, coma, and epilepsy. Direct electrical stimulation of parasympathetic nerves can activate the baroreflex, inducing a reduction of sympathetic nerve activity and reducing blood pressure by decreasing vascular resistance. Direct stimulation of the vagal parasympathetic fibers has been shown to reduce heart rate via the sympathetic nervous system. In addition, some research indicates that chronic stimulation of the vagus nerve may be of protective myocardial benefit following cardiac ischemic insult.

The ability to activate or stimulate single axons or small groups of axons (nerve bundles) within a common nerve trunk without stimulating other portions of the nerve has been referred to as selective activation. Related to selective activation is the ability to selectively sense and record activity from a single or small group of axons. Selective activation and recording are achievable through complex practices such as current steering for stimulating or the use of inter-fascicular electrodes for stimulating or recording. Another, less complex, method of achieving selective activation and recording involves the use of selective geometries. Neural stimulation electrodes presently used for selective activation of peripheral nerves include intraneural wire and silicon array electrodes, epineural electrodes, and multiple contact nerve cuff electrodes. These electrodes can, both in implantation and chronic use, cause mechanical irritation or insult due to the fragility of the neural tissue to be stimulated.

SUMMARY

The above-mentioned problems and others not expressly discussed herein are addressed by the present subject matter and will be understood by reading and studying this specification.

Disclosed herein, among other things, is a vascularly stabilized electrode assembly. An embodiment of the electrode assembly includes a body adapted to at least partially encompass a blood vessel and a nerve proximate to the blood vessel. The electrode assembly also includes at least one electrode along at least a portion of the body. The at least one electrode is adapted to be electrically connected to a neural stimulator. According to an embodiment, the electrode assembly includes a spacer within the body, the spacer having a first and second end, the first end secured to an inside surface of the body and the second end adapted to pass between the vessel and the nerve and to be secured to the inside surface of the body.

Also disclosed herein is a vascularly stabilized sensor assembly. According to an embodiment, the assembly includes a body adapted to at least partially encompass a blood vessel and a nerve proximate to the blood vessel. The assembly also includes at least one sensor along at least a portion of the body. According to various embodiments, the assembly also includes a spacer within the body, the spacer having a first and second end, the first end secured to an inside surface of the body and the second end adapted to pass between the vessel and the nerve and to be secured to the inside surface of the body.

One aspect of this disclosure relates to a system for delivering neural stimulation therapy. According to one embodiment, the system includes at least one neural stimulation lead. The system also includes an electrode assembly connected to the at least one lead. The electrode assembly includes a body adapted to at least partially encompass a blood vessel and a nerve proximate to the blood vessel, at least one electrode along at least a portion of the body, the at least one electrode adapted to be electrically connected to a neural stimulator, and a spacer within the body, the spacer having a first and second end, the first end secured to an inside surface of the body and the second end adapted to pass between the vessel and the nerve and to be secured to the inside surface of the body. The system also includes an implantable medical device coupled to the at least one lead. The implantable device includes a neural stimulator and a controller to communicate with the neural stimulator, the controller being adapted to control the neural stimulator to deliver neural stimulation to at least a portion of the nerve.

Another aspect of this disclosure relates to a method for forming an electrode assembly. An embodiment of the method includes forming a body adapted to at least partially encompass a blood vessel and a nerve proximate to the blood vessel. The method also includes embedding at least one electrode along at least a portion of the body, the at least one electrode adapted to be electrically connected to a neural stimulator. The method further includes forming a spacer within the body, the spacer having a first and second end, the first end secured to an inside surface of the body and the second end adapted to pass between the vessel and the nerve and to be secured to the inside surface of the body.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

Figure 1:
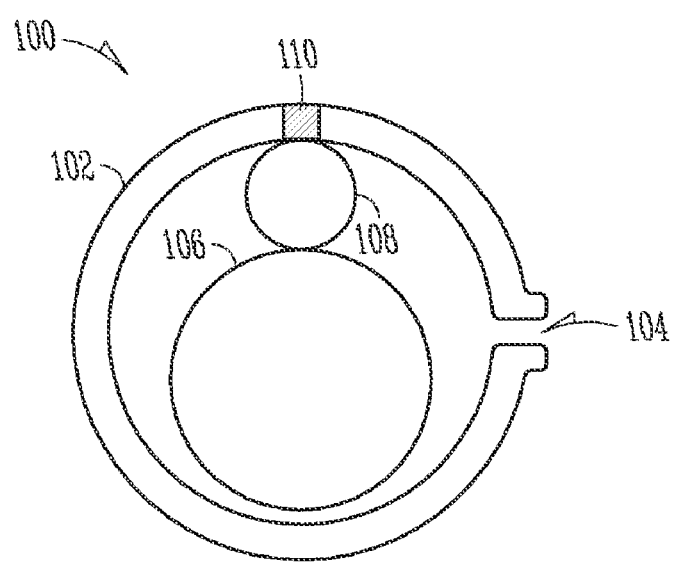
FIG. 1 is a cross-sectional side-view of a vascularly stabilized assembly, according to one embodiment.

The following detailed description refers to the accompanying drawings which show, by way of illustration, specific aspects and embodiments in which the present invention may be practiced. The various embodiments are not necessarily mutually exclusive, as aspects of one embodiment can be combined with aspects of another embodiment. These embodiments are described in sufficient detail to enable those skilled in the art to practice the invention. Other embodiments may be utilized and structural, logical, and electrical changes may be made without departing from the scope of the present invention.

A brief discussion of the physiology related to neurology is provided to assist the reader with understanding this disclosure. The automatic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal function and works with the somatic nervous system. Autonomic balance reflects the relationship between parasympathetic and sympathetic activity. A change in autonomic balance is reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies, for example.

An example of neural stimulation is baroreflex stimulation. Afferent nerve trunks, such as the vagus, aortic and carotid nerves, leading from the sensory nerve endings form part of a baroreflex pathway. Stimulating a baroreflex pathway inhibits sympathetic nerve activity, stimulates the parasympathetic nervous system and reduces systemic arterial pressure by decreasing peripheral vascular resistance and cardiac contractility. Neural stimulation of other neural targets is within the scope of the present disclosure, including stimulation of efferent and afferent pathways for parasympathetic and sympathetic nerves.

Stimulation of a vagus nerve trunk is used in a number of therapies. In an example, vagal nerve stimulation simultaneously increases parasympathetic tone and decreases sympathetic myocardial tone. In an example, a vagus nerve trunk is stimulated following cardiac ischemic insult. Increased sympathetic nervous activity following ischemia often results in increased exposure of the myocardium to epinephrine and norepinephrine. These catecholamines activate intracellular pathways within the myocytes, which lead to myocardial death and fibrosis. This effect is inhibited by stimulation of the parasympathetic nerves, such as vagus nerves. In an example, vagal stimulation from the SVC lowers heart rate, overall blood pressure, and left ventricular pressure. Stimulation of the vagal cardiac nerves following myocardial infarction, or in heart failure patients, can be beneficial in preventing further remodeling and arrhythmogenesis.

In other examples, neural stimulation is used to treat other conditions such as hypertrophic cardiomyopathy (HCM) or neurogenic hypertension, where an increase parasympathetic cardiac tone and reduction in sympathetic cardiac tone is desired. In another example, a bradycardia condition is treated by stimulating a sympathetic nerve trunk. In another example, the ionotropic state of the heart is increased by stimulating a sympathetic nerve trunk.

Selective activation (or selective stimulation) of nerve bundles within a nerve trunk has several benefits, including: allowing the ability to control one of a group of end organs; avoiding synergistic affects; decreasing the necessary stimulus amplitudes; and allowing coordinated movements or actions to mimic able-bodied persons. One advantage of the disclosed vascularly stabilized peripheral nerve cuff is that it improves access to nerve bundles for selective activation.

Another advantage of the disclosed assembly is its usefulness in providing Functional Electric Stimulation (FES). FES applications include selective recording of sensed neural activity and selective activation of portions of nerves to monitor and control muscular functions such as hand grasp, upper arm movements, standing and sitting prosthetics, and foot drop.

Neural stimulation electrodes presently used for activation of peripheral nerves, used in applications ranging from hand grasp to epilepsy, include intraneural wire and silicon electrodes, epineural electrodes, and multiple contact nerve cuff electrodes. These electrodes can, both in implantation and chronic use, cause mechanical irritation or insult due to the fragility of the neural tissue to be stimulated. The type of neural insult caused by these electrodes varies by design, but in some cases significant damage to the nerve can result. In some cases, the amount of insult to the nerve is transient, meaning the insult is dramatic in the acute phase (2-4 weeks) and recovers over time (1-2 months). A common type of neural insult is mechanical irritation to the nerve from the surgical procedure to isolate the nerve and place an electrode on the nerve. Chronic irritation after implantation is also common. An electrode assembly is needed which provides greater amounts of stability and less manipulation of the nerve during surgery.

Vascularly Stabilized Peripheral Nerve Cuff

The assembly disclosed herein is sometimes referred to as a vascularly stabilized peripheral nerve cuff, as the assembly surrounds both the nerve to be stimulated or sensed and an adjacent large blood vessel running parallel to the nerve, to provide stability for the assembly and reduce the nerve manipulation during and after implantation. This assembly also provides for more reliable and efficient chronic selective activation and/or selective sensing. As shown in the figures and discussed below, the disclosed assembly uses the local anatomy found in certain locations in the body to stabilize the interface between the nerve and the assembly using large vessels that are located adjacent the nerve. This assembly also reduces the amount of surgical isolation necessary in order to free the nerve. The vessel and nerve combination will be freed, and the mechanical properties of the vessel will sustain most of the manipulation.

FIG. 1 is a cross-sectional side-view of a vascularly stabilized assembly, according to one embodiment. The assembly 100 includes a body 102 with an opening 104 along a circumference, the opening 104 adapted to enable the body 102 to at least partially encompass a selected blood vessel 106 and an adjacent nerve 108 to provide stability during implantation and during delivery of neural stimulation or sensing. In an embodiment, the assembly 100 also includes at least one electrode 110 along at least a portion of the body 102, the at least one electrode 110 adapted to be electrically connected to a neural stimulator. According to an embodiment, the assembly includes at least one neural sensor along at least a portion of the body 102, the at least one sensor adapted to selectively sense neural activity of an axon or group of axons within the nerve. The assembly is adapted for selective recording, or recording of selectively sensed neural activity, in one embodiment. According to an embodiment, the assembly also includes a fastener adapted to close the opening to prevent separation from the vessel and nerve after implantation.

Figure 2A:
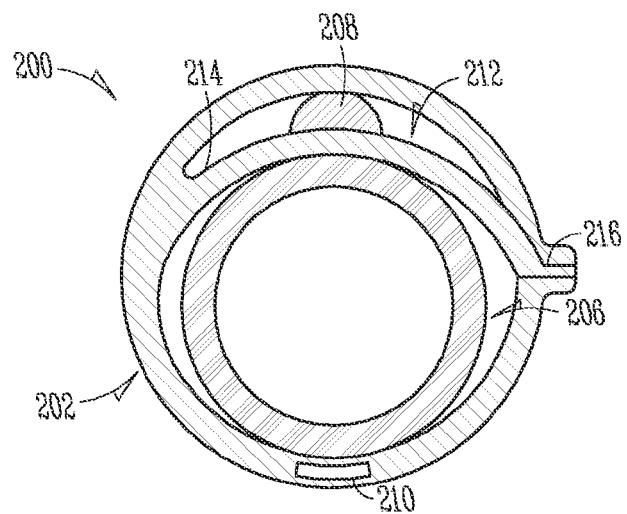
FIGS. 2A through 2H illustrate vascularly stabilized assemblies, according to various embodiments.

FIGS. 2A through 2H illustrate vascularly stabilized assemblies, according to various embodiments. FIG. 2A is a cross-sectional side-view of an assembly 200. The assembly 200 includes a body 202 adapted to at least partially encompass a blood vessel 206 and a nerve 208 proximate to the blood vessel. In an embodiment, the assembly 200 also includes at least one electrode 210 along at least a portion of the body. The at least one electrode 210 is adapted to be electrically connected to a neural stimulator. The assembly also includes a spacer 212 within the body, the spacer having a first and second end, the first end 214 secured to an inside surface of the body and the second end 216 adapted to pass between the vessel 206 and the nerve 208 and to be secured to the inside surface of the body.

According to one embodiment, the inside surface of the body includes an interior facing wall shaped to conform to the blood vessel and the nerve. The inside surface of the body is sized to securely encompass the vessel and nerve in an embodiment. The inside surface of the body is sized to tightly encompass the vessel and nerve in an embodiment. The inside surface of the body is sized to hold in place the vessel and nerve in an embodiment. The spacer may have a variety of geometries. In one embodiment, the spacer includes a member having an arc-like shape. In one embodiment, the spacer is tapered to more easily pass between the vessel and nerve.

According to an embodiment, the body has a hollow, cylindrical shape. According to one embodiment, the body includes an opening, the opening adapted to enable the body to at least partially encompass the blood vessel and the nerve. The opening may be along a circumference. In one embodiment, the assembly may also include a fastener adapted to close the opening to prevent separation from the vessel and nerve after implantation. The fastener may be further adapted to secure the second end of the spacer to the inside surface of the body, in one embodiment. In one embodiment, the fastener includes a wire spiral. In one embodiment, the fastener includes sutures. In various embodiments, the fastener includes a clasp or self-closing mechanism.

The selected blood vessel includes a carotid artery in one embodiment. The selected blood vessel includes an internal jugular vein in an embodiment. Other vessels are within the scope of this disclosure. The adjacent nerve includes a vagal nerve in an embodiment. Other nerves are within the scope of this disclosure.

The body 202 is constructed of an insulating biocompatible material in various embodiments. An example of an insulating biocompatible material is silicone. A biocompatible silicon elastomer provides a flexible and reliable material to interface with the nerve and vessel. In one embodiment, the body wraps around the nerve and the vessel one time, and in other embodiments the body wraps around the nerve and vessel multiple times. In an embodiment, the at least one electrode 210 is electrically connected to the neural stimulator via a neural stimulation lead. In another embodiment, the at least one electrode 210 is electrically connected to the neural stimulator at least partially via a wireless connection. In one embodiment, the assembly includes an attached pulse output circuit with an energy source, which is wirelessly connected to the neural stimulator which acts as a controller. The electrodes include a window to the nerve/body interface for electrode or electrolyte transfer, according to various embodiments.

Figure 2B:
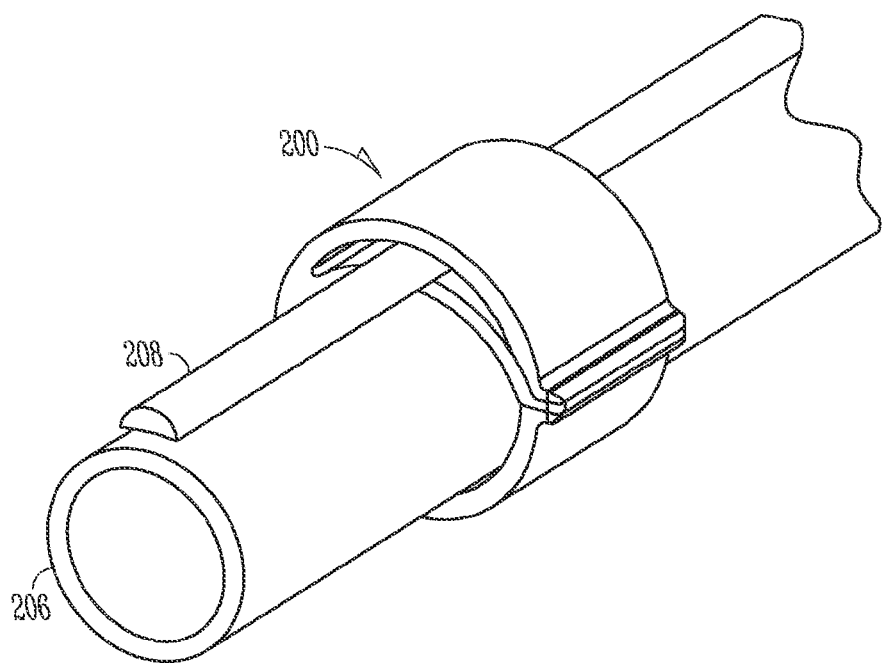

The spacer 212, or insert, resides between the nerve 208 and vessel 206 and allows for additional electrical contacts for providing selective activation to the nerve 208. Those of skill in the art will appreciate that specific nerve bundles (or fascicles) can more easily be targeted for selective activation or selective sensing in this geometry, as neural fibers of interest are brought closer to the electrode(s). Selective activation or sensing can then be achieved using simple monophasic low current amplitude stimuli, or using field steering techniques. In addition, selective activation or sensing can be achieved chronically in this setting, and an increased area for electrical contact placement is provided. In one embodiment, the assembly 200 is adapted to sense blood pressure in the blood vessel, and blood pressure parameters, and other parameters that are associated with cardiac or systemic compliance. The assembly includes pressure sensors to support this function, in an embodiment. In one embodiment, the assembly 200 is adapted to include a drug eluting polymer. Various types of medications can be administered using the drug eluting polymer assembly, including anti-inflammatory drugs to reduce the inflammatory response from the body and nerve growth factor to help repair injured axons within the nerve. FIG. 2B is a perspective view of the assembly 200 shown in FIG. 2A.

Figure 2C:
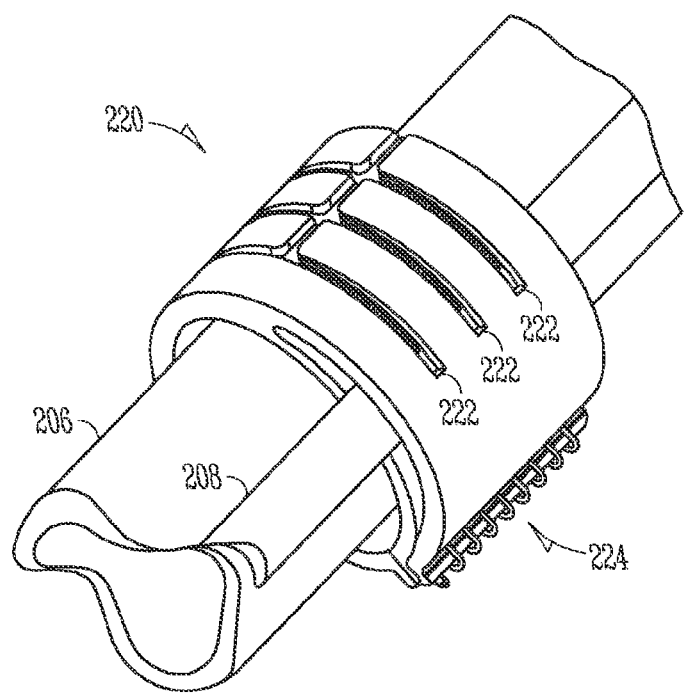

FIG. 2C illustrates an embodiment of the assembly 200 of FIG. 2A. In this embodiment, the assembly 220 includes a series of electrical contacts 222 aligned with the nerve. These electrical contacts, or electrodes, can be placed in many locations around the nerve and vessel to apply pseudo unipolar stimulation, selective bipolar stimulation, current steering techniques and other stimulation waveforms to promote device longevity and neural safety. This assembly also includes a spiral wire fastener 224 to close the opening in the body of the assembly 220. FIG. 2E illustrates further views of the assembly 220 shown in FIG. 2C.

Figure 2D:
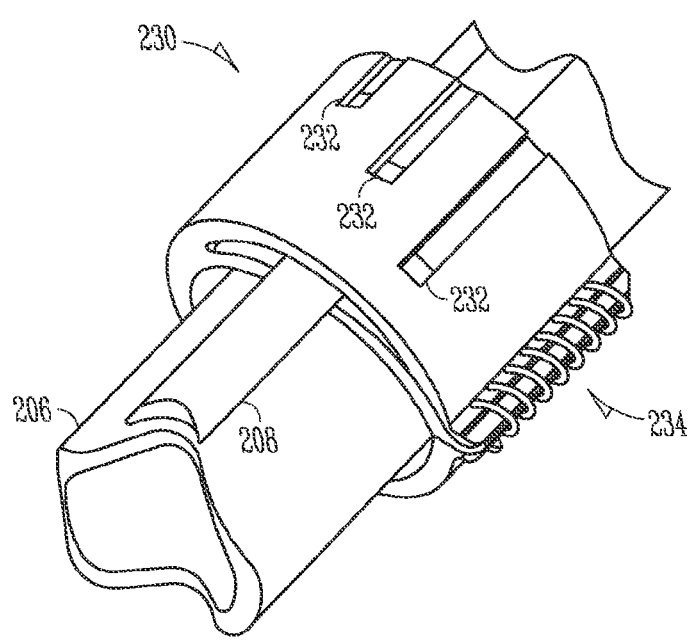
Figure 2E:
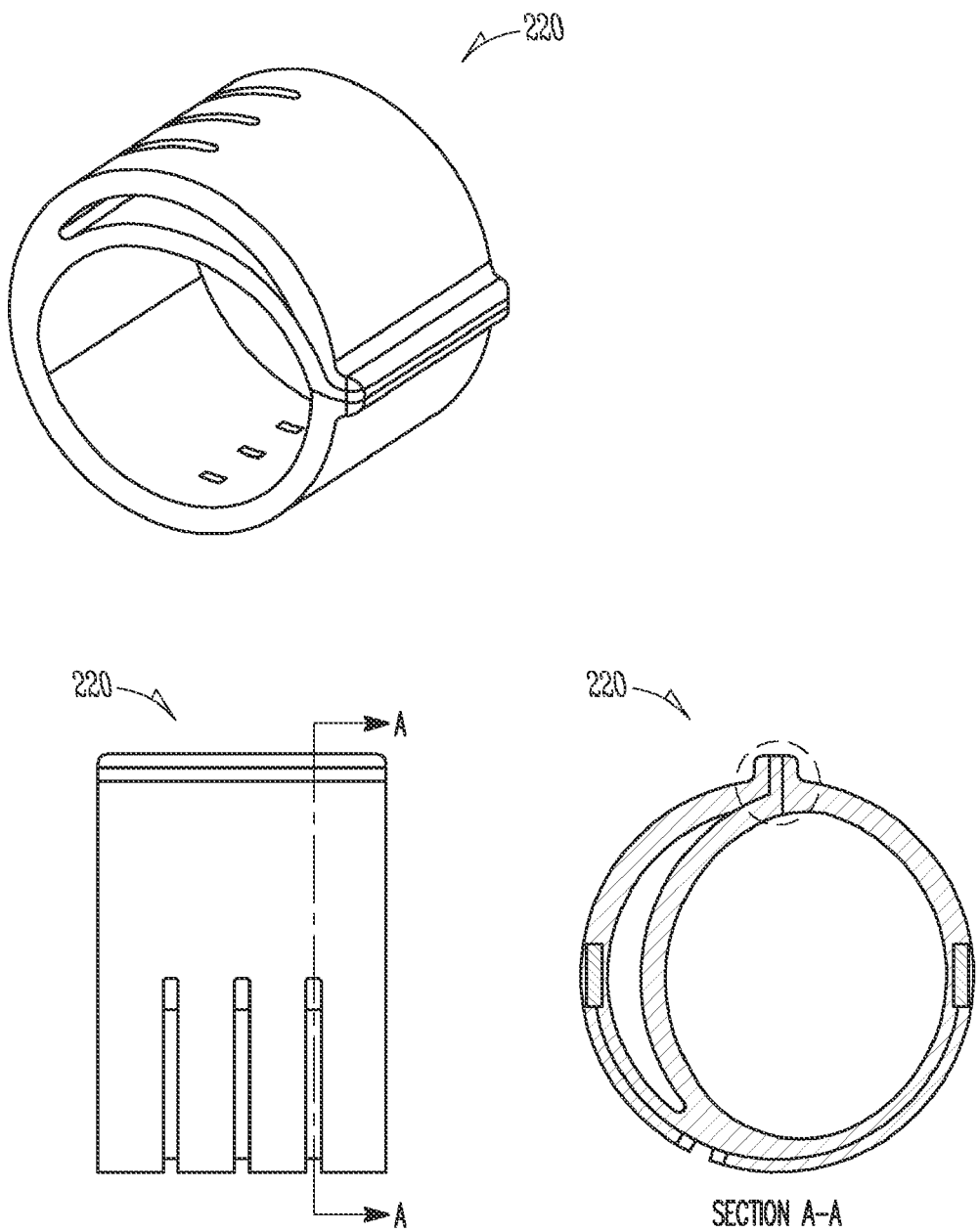
Figure 2F:
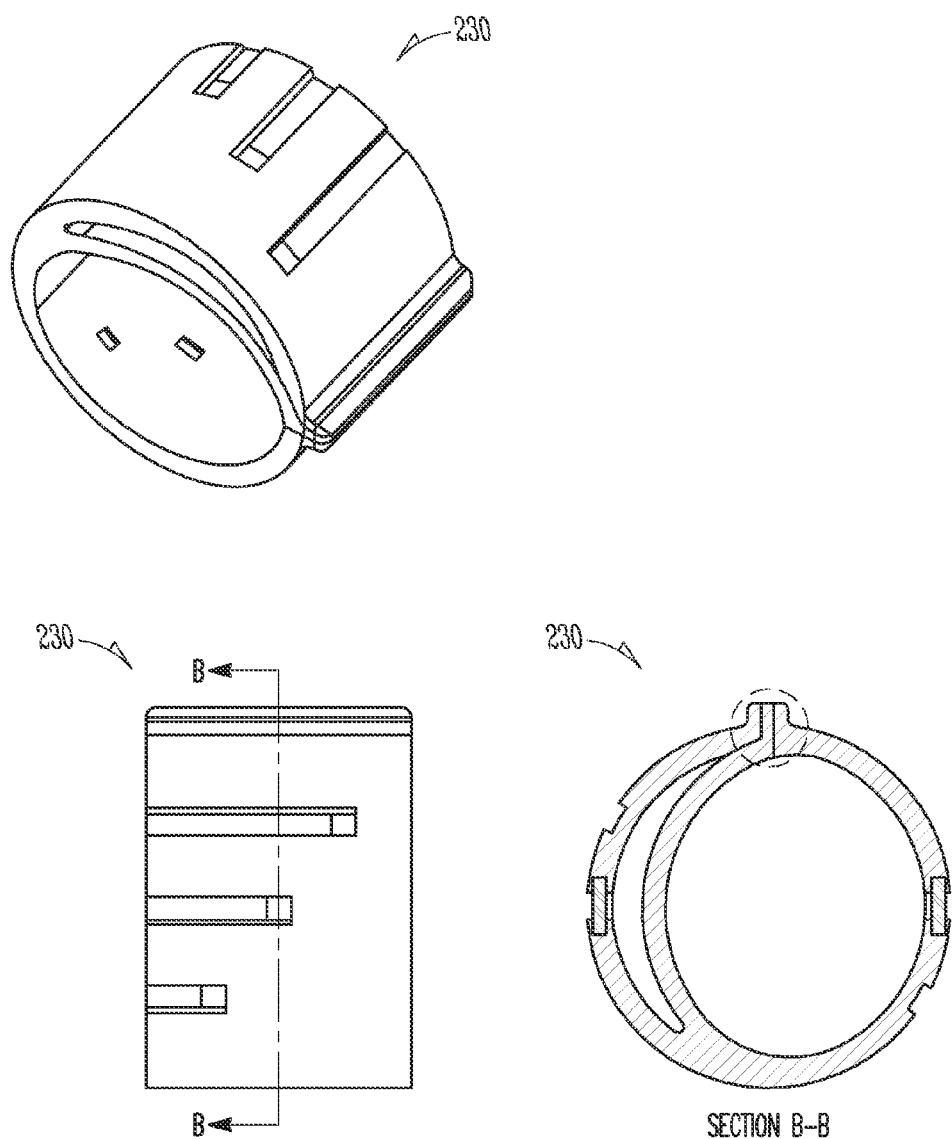

FIG. 2D illustrates an embodiment of the assembly 200 of FIG. 2A. In this embodiment, the assembly 230 includes a series of electrical contacts 232 that are offset from each other with respect to the nerve. As mentioned, these electrical contacts, or electrodes, can be placed in many locations around the nerve and vessel to apply pseudo unipolar stimulation, selective bipolar stimulation, current steering techniques and other stimulation waveforms to promote device longevity and neural safety. This assembly 230 utilizes the geometry of the nerve to enable selective activation. This assembly also includes a spiral wire fastener 234 to close the opening in the body of the assembly 230. FIG. 2F illustrates further views of the assembly 230 shown in FIG. 2D.

Figure 2G:
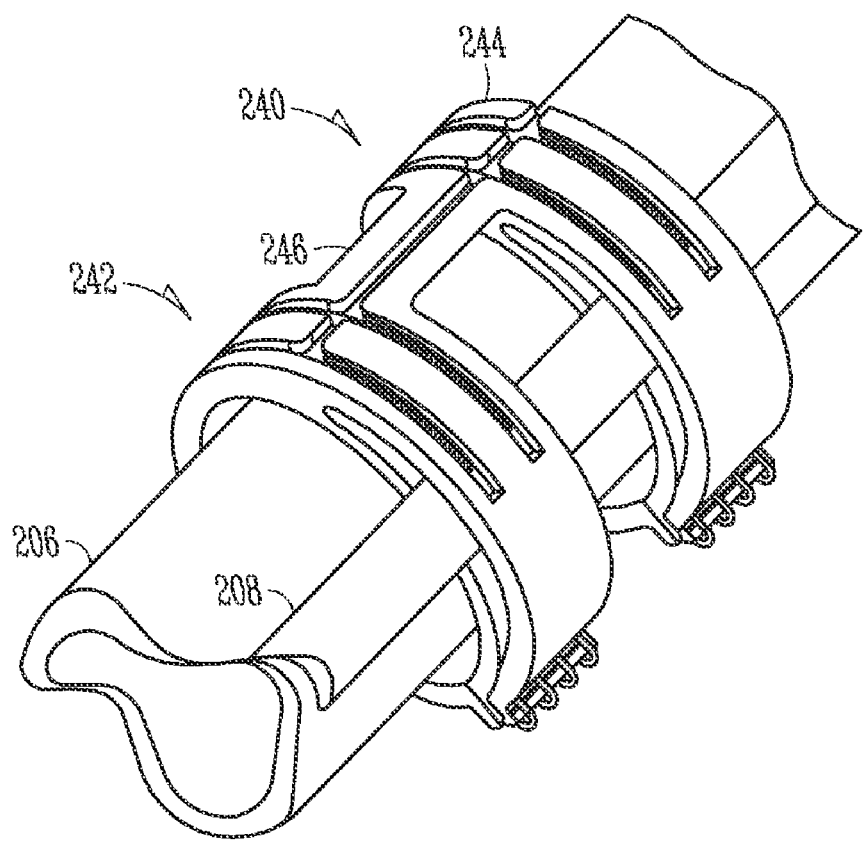
Figure 2H:
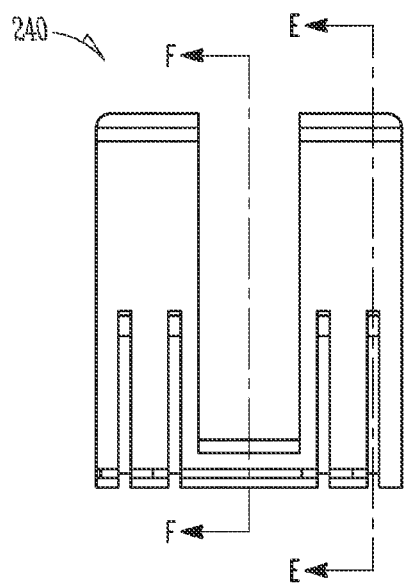
Figure 2H:
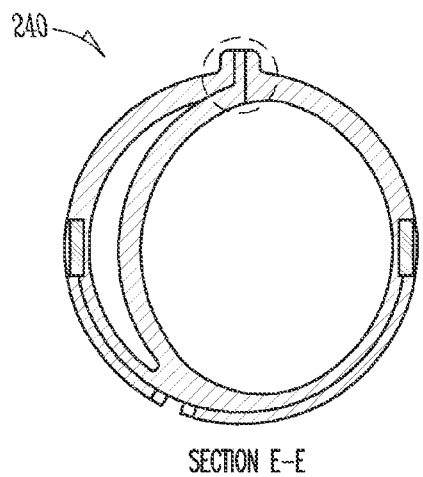
Figure 2H:
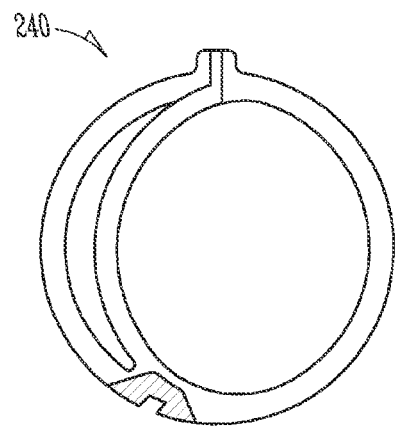

FIG. 2G illustrates an embodiment including multiple assemblies 200 of FIG. 2A. A system 240 is depicted including a first assembly 242 and a second assembly 244 electrically connected to the first assembly along a stabilizer bar 246. The first assembly 242 and the second assembly 244 include a body adapted to at least partially encompass a blood vessel and a nerve proximate to the blood vessel, at least one electrode or sensor along at least a portion of the body, the at least one electrode adapted to be electrically connected to a neural stimulator, and a spacer within the body, the spacer having a first and second end, the first end secured to an inside surface of the body and the second end adapted to pass between the vessel and the nerve and to be secured to the inside surface of the body. Other embodiments of systems including a third, a fourth, and an Nth assembly further connected along with the first and second assemblies are within the scope of this disclosure. According to various embodiments, other connection means are used to connect the assemblies, including support members and portions of leads. FIG. 2H illustrates further views of the system 240 shown in FIG. 2G.

As mentioned, the disclosed assembly provides for more reliable and efficient chronic selective activation and/or selective sensing. The disclosed assembly is therefore useful in providing Functional Electric Stimulation (FES). FES applications include selective recording of sensed neural activity and selective activation of portions of nerves to monitor and control muscular functions such as hand grasp, upper arm movements, standing and sitting prosthetics, and foot drop.

System for Delivering Neural Stimulation

Figure 3:
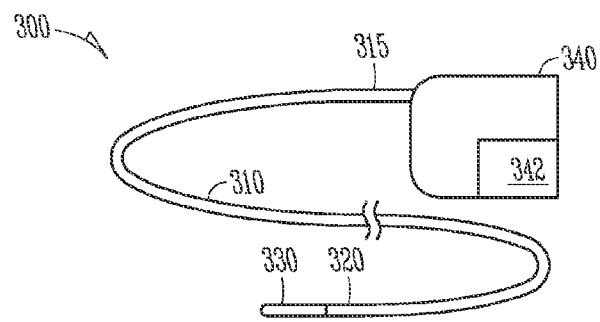
FIG. 3 illustrates a lead and an implantable medical device (IMD), according to one embodiment.

FIG. 3 illustrates a lead and an implantable medical device (IMD), according to one embodiment. Lead 300 includes a flexible lead body 310 extending from a proximal end 315 to a distal end 320. An electrode assembly 330, such as the assemblies described with respect to FIGS. 1-2H above, is proximate the distal end 320 of lead body 310. In various embodiments, the electrode assembly is connected along other portions of the lead.

Lead 300 is coupled to an implantable medical device (IMD) 340, or pulse generator. Lead 300 includes conductors, such as coiled conductors that electrically couple pulse generator 340 to electrode assembly 330. Accordingly, implantable medical device 340 can deliver a stimulation signal to via the distal portion. The lead further includes outer insulation to insulate the conductor. The system can include a unipolar system with the case acting as an electrode or a bipolar system with a pulse between two distally located electrodes.

In one embodiment, implantable medical device 340 includes hardware, circuitry and software to perform neural stimulation functions, and includes controller circuitry 342. The controller circuitry 342 is capable of being implemented using hardware, software, and combinations of hardware and software. For example, according to various embodiments, the controller circuitry 342 includes a processor to perform instructions embedded in a memory to perform functions associated with neural stimulation, including selective activation.

Figure 4:
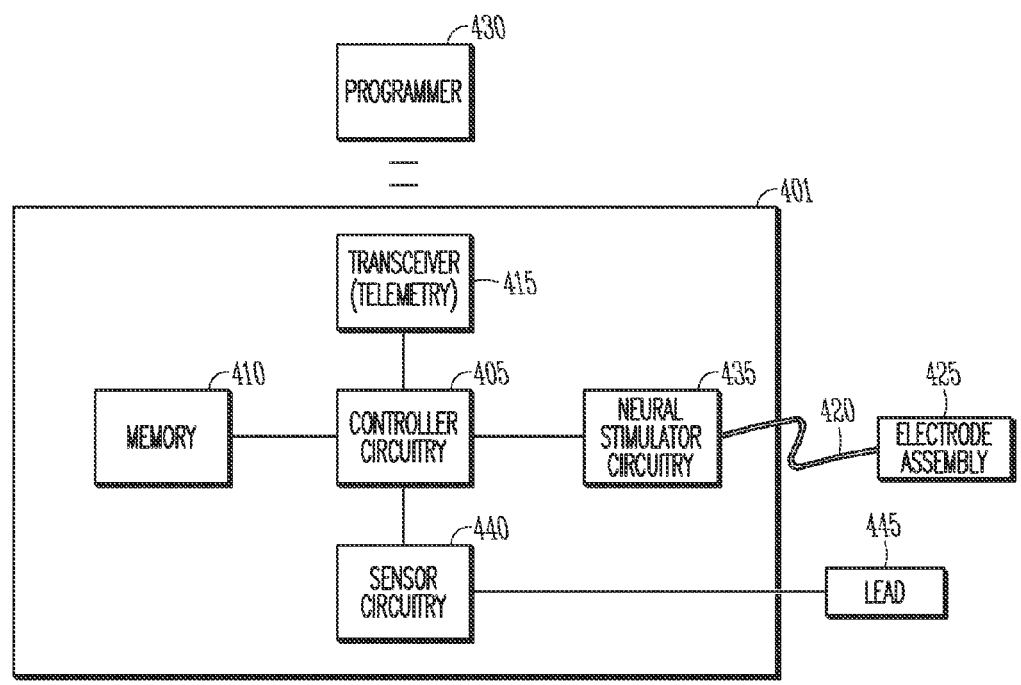
FIG. 4 is a schematic illustration of an implantable system for delivering neural stimulation, according to one embodiment.

FIG. 4 is a schematic illustration of an implantable system for delivering neural stimulation, according to one embodiment. The system includes an implantable device 401, an electrical lead 420 coupled to the implantable device 401, and an electrode assembly 425. The implantable device includes a controller circuit 405, a memory circuit 410, a telemetry circuit 415, and a neural stimulation circuit 435. The controller circuit 405 is operable on instructions stored in the memory circuit to deliver an electrical neural stimulation therapy. Therapy is delivered by the neural stimulation circuit 435 through the lead 420 and the electrode assembly 425. The telemetry circuit 415 allows communication with an external programmer 430. The illustrated system also includes optional sensor circuitry 440 that is coupled to a lead 445. The controller circuit 405 processes sensor data from the sensor circuitry and delivers a therapy responsive to the sensor data.

Figure 5:
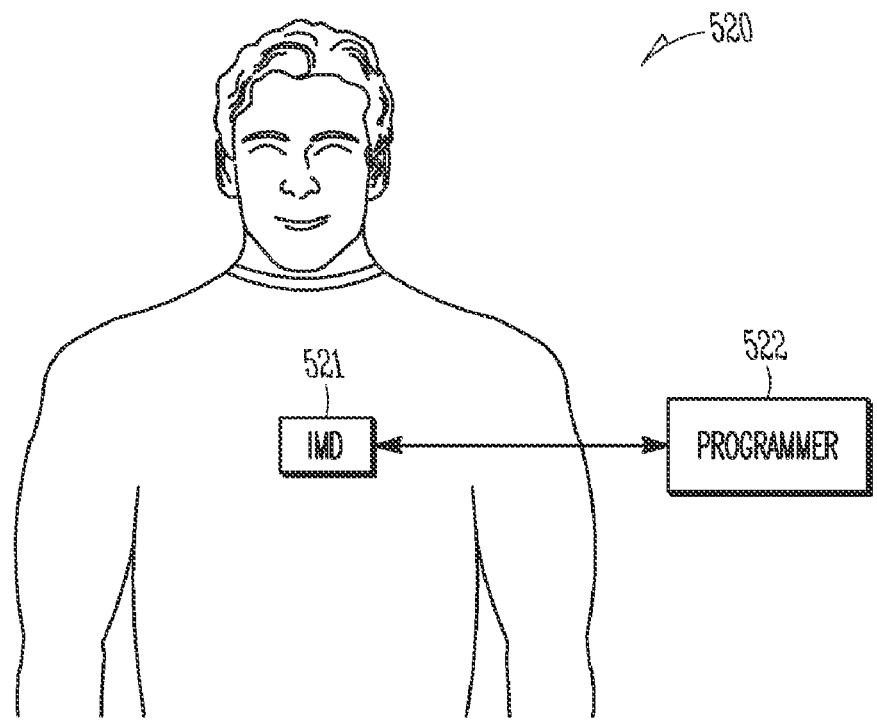
FIG. 5 illustrates a system including an implantable medical device (IMD) and a programmer, according to one embodiment.

FIG. 5 illustrates a system 520 including an implantable medical device (IMD) 521 and a programmer 522, according to one embodiment. Various embodiments of the IMD 521 include neural stimulator functions only, and various embodiments include a combination of neural stimulation and cardiac rhythm management functions. The programmer 522 and the IMD 521 are capable of wirelessly communicating data and instructions. In various embodiments, for example, the programmer 522 and IMD 521 use telemetry coils to wirelessly communicate data and instructions. Thus, the programmer can be used to adjust the programmed therapy provided by the IMD 521, and the IMD can report device data (such as battery and lead resistance) and therapy data (such as sense and stimulation data) to the programmer using radio telemetry, for example. According to various embodiments, the IMD 521 selectively stimulates nerve bundles using the electrode assembly disclosed in FIGS. 2A-2H described above. According to various embodiments, the IMD 521 includes a sensor to sense ANS activity. Such a sensor can be used to perform feedback in a closed loop control system. For example, various embodiments sense surrogate parameters, such as respiration and blood pressure, indicative of ANS activity. According to various embodiments, the IMD further includes cardiac stimulation capabilities, such as pacing and defibrillating capabilities in addition to the capabilities to stimulate nerve bundles and/or sense ANS activity.

Figure 6:
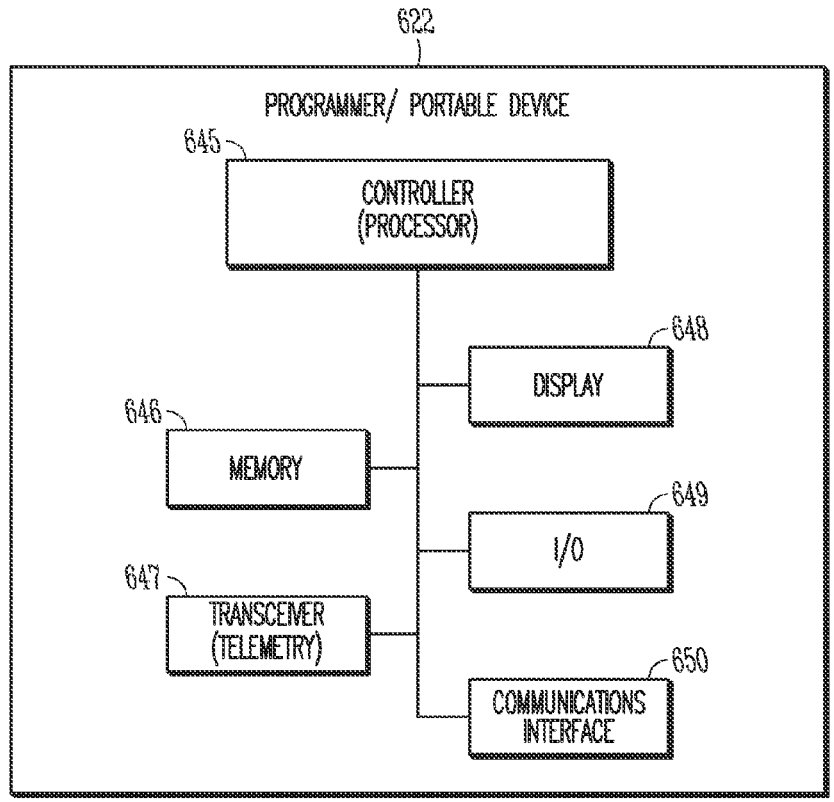
FIG. 6 illustrates a programmer such as illustrated in the system of FIG. 5 or other external device to communicate with the implantable medical device(s), according to one embodiment.

FIG. 6 illustrates a programmer 622, such as the programmer 522 illustrated in the system of FIG. 5 or other external device to communicate with the implantable medical device(s), according to one embodiment. An example of another external device includes Personal Digital Assistants (PDAs) or personal laptop and desktop computers in an Advanced Patient Management (APM) system. The illustrated device 622 includes controller circuitry 645 and a memory 646. The controller circuitry 645 is capable of being implemented using hardware, software, and combinations of hardware and software. For example, according to various embodiments, the controller circuitry 645 includes a processor to perform instructions embedded in the memory 646 to perform a number of functions, including communicating data and/or programming instructions to the implantable devices. The illustrated device 622 further includes a transceiver 647 and associated circuitry for use to communicate with an implantable device. Various embodiments have wireless communication capabilities. For example, various embodiments of the transceiver 647 and associated circuitry include a telemetry coil for use to wirelessly communicate with an implantable device. The illustrated device 622 further includes a display 648, input/output (I/O) devices 649 such as a keyboard or mouse/pointer, and a communications interface 650 for use to communicate with other devices, such as over a communication network.

Method for Forming an Electrode Assembly

Figure 7:
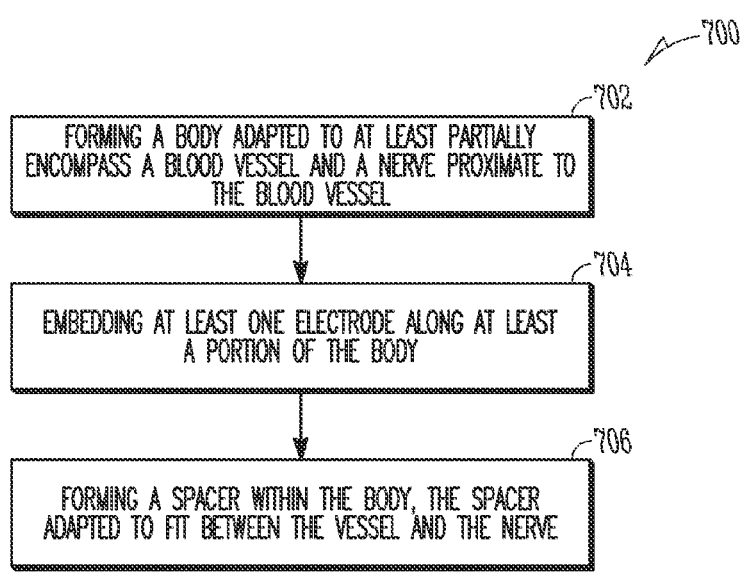
FIG. 7 illustrates a flow diagram of a method for forming an electrode assembly, according to one embodiment.

FIG. 7 illustrates a flow diagram of a method for forming an electrode assembly, according to one embodiment. The method 700 includes forming a body adapted to at least partially encompass a blood vessel and a nerve proximate to the blood vessel, at 702. The method also includes embedding at least one electrode along at least a portion of the body, the at least one electrode adapted to be electrically connected to a neural stimulator, at 704. The method further includes forming a spacer within the body, the spacer having a first and second end, the first end secured to an inside surface of the body and the second end adapted to pass between the vessel and the nerve and to be secured to the inside surface of the body, at 706. According to an embodiment, the method also includes forming a fastener adapted to prevent separation from the vessel and nerve after implantation.

According to various embodiments, the inside surface of the body is formed to conform to the blood vessel and the nerve. The body may have a variety of geometries, and is formed with a hollow, cylindrical shape in an embodiment. The spacer may have a variety of geometries, and is formed with an arc-like shape in an embodiment.

According to an embodiment, the multiple stimulating contacts are imbedded parallel to one another along the body. According to an embodiment, the multiple stimulating contacts are imbedded offset from one another along the body.

According to various embodiments, forming a hollow, cylindrical body includes forming the body with a biocompatible material. According to an embodiment, the at least one electrode includes a stimulating contact constructed from platinum. According to an embodiment, the at least one electrode includes a stimulating contact constructed from stainless steel. According to an embodiment, the at least one electrode includes a stimulating contact constructed from IROX™ (iridium oxide-coated titanium). According to an embodiment, the at least one electrode includes a stimulating contact constructed from platinum and iridium. According to an embodiment, the at least one electrode includes multiple stimulating contacts of different lengths parallel to each other along the body. The disclosed method takes advantage of cervical anatomy to form an electrode assembly for positioning neural tissue where simple stimulation protocols can be used to selectively activate small sub-populations of fibers, according to various embodiments.

Electrode Placement Targets

Figure 8A:
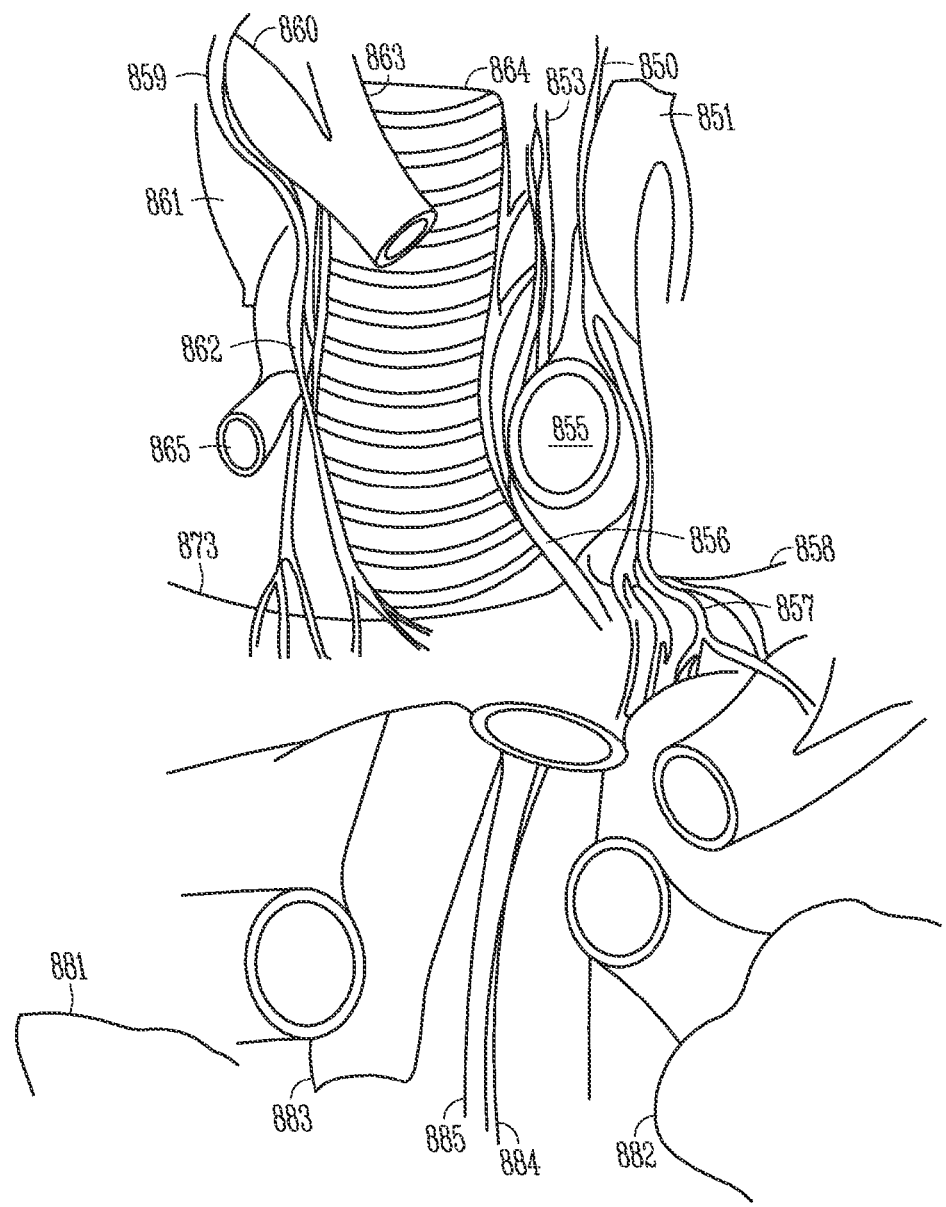
FIGS. 8A and 8B are illustrations of blood vessels and nerves used by the present system, according to various embodiments.
Figure 8B:
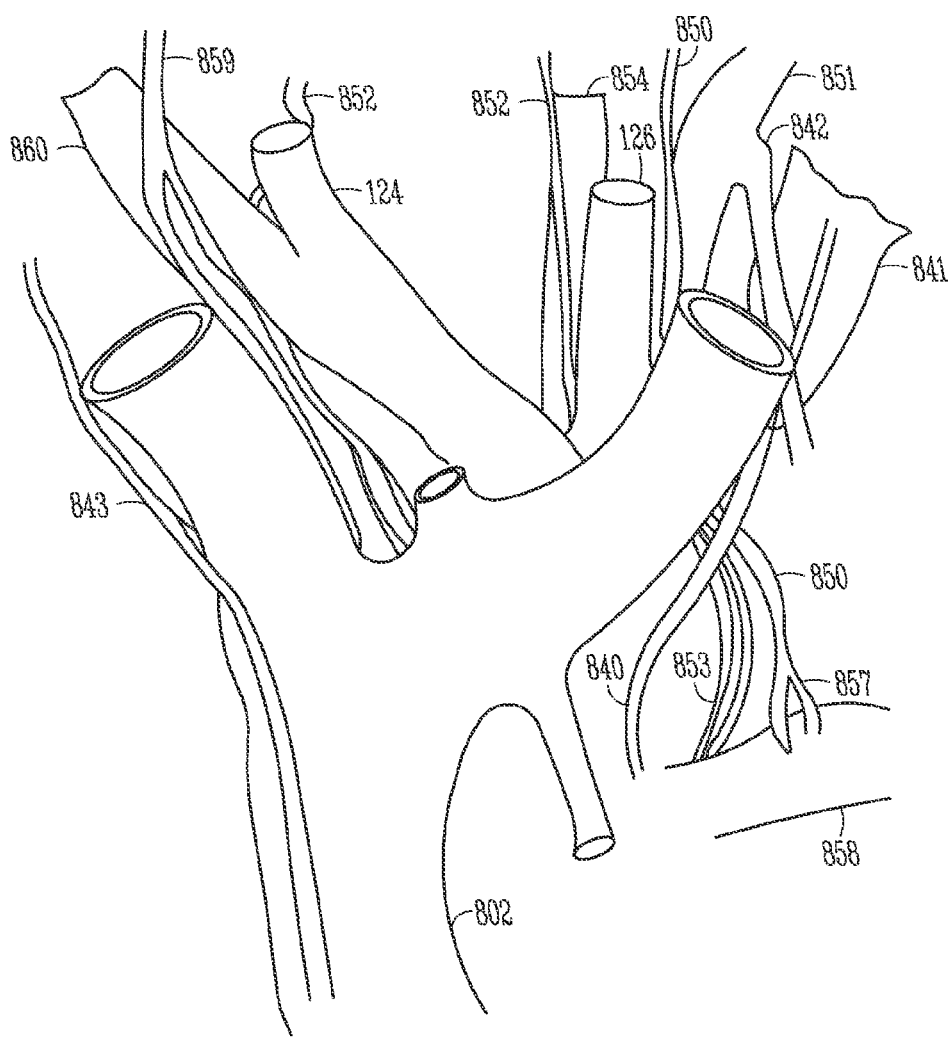

FIGS. 8A and 8B are illustrations of blood vessels and nerve trunks used by the present system, according to various embodiments. FIG. 8A shows left vagus nerve 850 extending next to a subclavian artery 851. Various nerves extend around the arch of the aorta 855. Vagus nerve 850 also extends past the ligamentum arteriosum 856. The anterior pulmonary plexus 857 crosses the left pulmonary artery 858. Right vagus nerve 859 extends past a subclavian artery 860 and the cupola of pleura 861. Cardiac nerves 862 extend past the brachiocephalic trunk 863 near the trachea 864. Cardiac nerves 862 also extend past the arch of an azygos vein 865 to the right pulmonary artery 873. In the lower portion of FIG. 8A appear the right lung 881, left lung 882, esophagus 883, a lower portion 884 of the left vagus nerve 850, and a lower portion 885 of the aorta. FIG. 8B shows a left phrenic nerve 840 extending past a cupola of pleura 841, an internal thoracic artery 842, and left pulmonary artery 858. Vagus nerve 850, recurrent laryngeal nerves 852, cardiac nerves 853, and the anterior pulmonary plexus 857 extend near the left pulmonary artery 858 and ligamentum arteriosum.

Figure 8C:
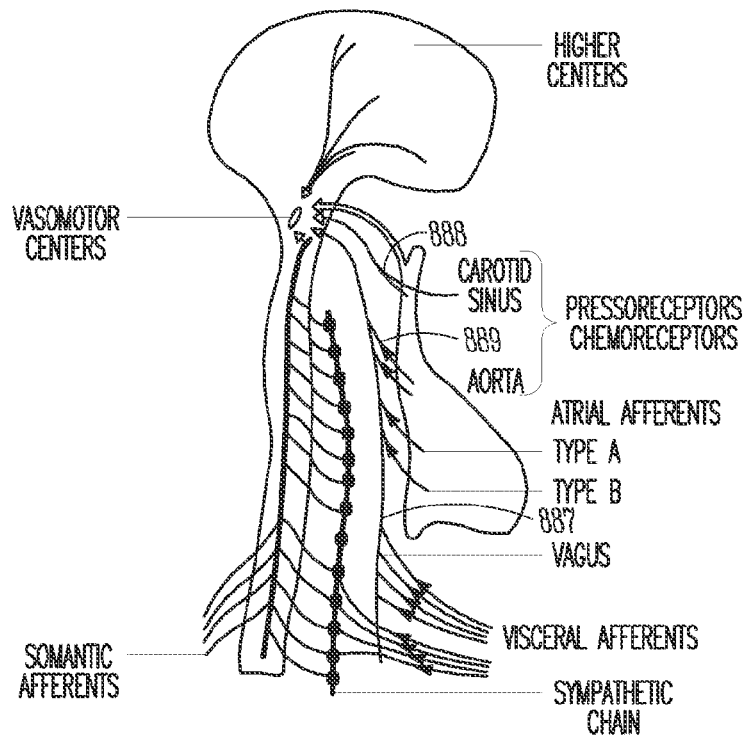
FIGS. 8C and 8D show neural pathways targeted by the present system, according to various embodiments.
Figure 8D:
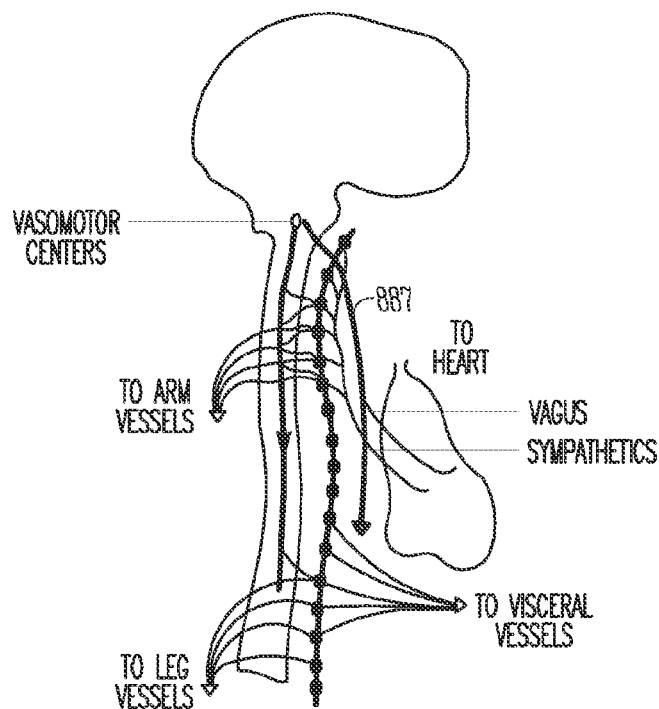

FIGS. 8C and 8D show neural pathways targeted by the present system, according to various embodiments. FIG. 8C generally illustrates afferent nerves to vasomotor centers. An afferent nerve conveys impulses toward a nerve center. A vasomotor center relates to nerves that dilate and constrict blood vessels to control the size of the blood vessels. FIG. 8D generally illustrates efferent nerves from vasomotor centers. An efferent nerve conveys impulses away from a nerve center. Afferent and efferent nerves can be stimulated with the disclosed electrode assemblies.

Figure 8E:
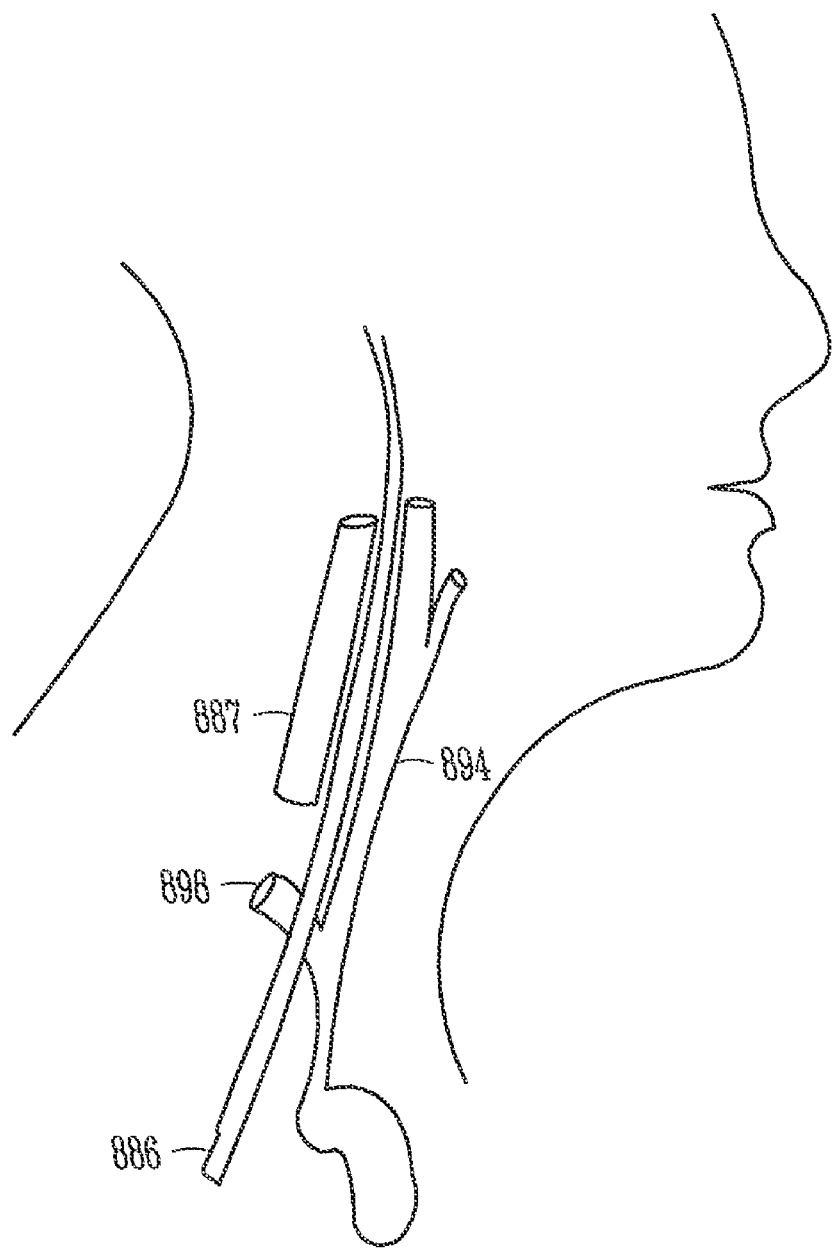
FIG. 8E is an illustration of an internal jugular vein near a vagus nerve for chronic implantation of the present apparatus, according to various embodiments.

FIG. 8E is an illustration of an internal jugular vein 887 near a vagus nerve 886 for chronic implantation of the present apparatus, according to various embodiments. A common carotid artery 894 and subclavian artery 898 are also shown in FIG. 8E. In other examples, nerve trunks innervating other organs, such as the lungs or kidneys are stimulated.

The vagus nerve includes a left and right vagus nerve. The right vagus nerve passes anterior to the subclavian artery, breaks up into pulmonary plexus posterior to root of the right lung, refers and then breaks up into esophageal and cardiac plexuses. The left vagus nerve passes to the left of the aortic arch and posterior to the root of the left lung, giving pulmonary, esophageal and cardiac plexuses. The described electrode assemblies provide stabilized means to provide vagal stimulation, including selective vagal activation. Vagal nerve stimulation (VNS) can be used with the following control measures: R-R interval; P-R interval; Q-T interval; systolic pressure; diastolic pressure; MAP; stroke volume; respiratory rate; tidal volume; temperature; activity level; EEG; EMG; wake/sleep state; apnea/hypopnea Index; ENG; and EOG. Those of skill in the art will recognize that other control measures can be associated with VNS using the disclosed system.

While the above description discusses utilization of the present system with the vagal nerve, the system can be used anywhere in a human body where a major vessel is running next to a nerve. Examples include but are not limited to the femoral nerve and the ulna or median nerve, or other location where a vessel lies in close proximity to a nerve. In addition, the system can be used to sense and measure vessel characteristics.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description.

The scope of the present subject matter should be determined with reference to the appended claims, along with the full scope of equivalents to which such claims are entitled.

What is claimed is:

1. An electrode assembly, comprising:
   an electrode body adapted to chronically and at least partially encompass a blood vessel and a nerve proximate to the blood vessel after implantation of the assembly, wherein the body has a shape to conform to the blood vessel without restricting blood flow through the vessel;
   at least one neural stimulation electrode along at least a portion of the body, the at least one electrode adapted to be electrically connected to a neural stimulator and configured for use to stimulate the nerve; and
   a spacer within the body, the spacer having a first and second end, the first end secured to an inside surface of the body and the second end adapted to pass between the vessel and the nerve and to be secured to the inside surface of the body.

2. The electrode assembly of claim 1, wherein the inside surface of the body includes an interior facing wall shaped to conform to the blood vessel and the nerve.

3. The electrode assembly of claim 1, wherein the spacer includes a member having an arc-like shape.

4. The electrode assembly of claim 1, wherein the body has a hollow, cylindrical shape with an opening along a circumference, the opening adapted to enable the body to at least partially encompass the blood vessel and the nerve.

5. The electrode assembly of claim 4, further comprising a fastener adapted to close the opening to prevent separation from the vessel and nerve after implantation.

6. The electrode assembly of claim 5, wherein the fastener is further adapted to secure the second end of the spacer to the inside surface of the body.

7. The electrode assembly of claim 1, wherein the blood vessel includes a carotid artery.

8. The electrode assembly of claim 1, wherein the blood vessel includes an internal jugular vein.

9. The electrode assembly of claim 1, wherein the nerve includes a vagal nerve.

10. The electrode assembly of claim 1, further comprising:
    at least one sensor along at least a portion of the body.

11. The electrode assembly of claim 10, wherein the assembly is adapted to provide Functional Electric Stimulation (FES).

12. The electrode assembly of claim 1, wherein the at least one electrode is adapted to be electrically connected to the neural stimulator at least partially via a wireless connection.

13. The electrode assembly of claim 1, wherein the blood vessel has a diameter and the nerve has a diameter, and the diameter of the blood vessel is larger than the diameter of the nerve.

14. The electrode assembly of claim 1, wherein:
    the body and the spacer define a first opening in the electrode assembly to receive the blood vessel, wherein the body and the spacer are configured to secure the electrode assembly to the blood vessel when the blood vessel is in the first opening; and
    the body and the spacer define a second opening in the electrode assembly to receive the nerve,
    wherein, after implantation of the assembly, the nerve is chronically in the second opening and the blood vessel is chronically in the first opening and blood continues to flow through the blood vessel while the blood vessel is in the first opening.

15. The electrode assembly of claim 14, wherein:
    the body and the spacer are configured to provide an open position for the first opening to receive the blood vessel in the first opening, and to provide a close position for the first opening to secure the electrode assembly to the blood vessel; and
    the body and the spacer are configured to provide an open position for the second opening to receive the nerve in the second opening, and to provide a close position for the second opening to secure the electrode assembly to the nerve.

16. An assembly, comprising:
    an electrode body adapted to at least partially encompass a blood vessel and a nerve proximate to the blood vessel after implantation of the assembly, wherein the body has a shape to conform to the blood vessel without restricting blood flow through the vessel;
    at least one sensor along at least a portion of the body; and
    a spacer within the body, the spacer having a first and second end, the first end secured to an inside surface of the body and the second end adapted to pass between the vessel and the nerve and to be secured to the inside surface of the body.

17. The assembly of claim 16, wherein the at least one sensor is adapted to selectively sense neural activity of an axon or group of axons within the nerve.

18. The assembly of claim 17, wherein the assembly is adapted for recording of selectively sensed neural activity.

19. The assembly of claim 16, wherein the at least one sensor is adapted to sense blood pressure in the blood vessel.

20. The assembly of claim 16, further comprising:
    at least one electrode along at least a portion of the body, the at least one electrode adapted to be electrically connected to a neural stimulator.

21. A system, comprising:
    at least one neural stimulation lead;
    an electrode assembly connected to the at least one lead, the electrode assembly including:
        an electrode body adapted to at least partially encompass a blood vessel and a nerve proximate to the blood vessel after implantation of the assembly, wherein the body has a shape to conform to the blood vessel without restricting blood flow through the vessel;
        at least one neural stimulation electrode along at least a portion of the body, the at least one electrode adapted to be electrically connected to a neural stimulator and configured for use to stimulate the nerve; and
        a spacer within the body, the spacer having a first and second end, the first end secured to an inside surface of the body and the second end adapted to pass between the vessel and the nerve and to be secured to the inside surface of the body; and
    an implantable medical device, coupled to the at least one lead, the implantable device including:
        a neural stimulator; and
        a controller to communicate with the neural stimulator, the controller being adapted to control the neural stimulator to deliver neural stimulation to at least a portion of the nerve.

22. The system of claim 21, wherein the electrode assembly further includes:
    a fastener adapted to close the opening to prevent separation from the vessel and nerve after implantation.

23. The system of claim 22, wherein the fastener is further adapted to secure the second end of the spacer to the inside surface of the body.

24. The system of claim 21, wherein the electrode assembly is adapted to sense blood pressure in the blood vessel.

25. The system of claim 21, wherein the electrode assembly is adapted to include a drug eluding polymer.

26. The system of claim 21, further comprising:
a second electrode assembly electrically connected to the electrode assembly along a stabilizer bar, the second electrode assembly including:
a body adapted to at least partially encompass a blood vessel and a nerve proximate to the blood vessel after implantation of the assembly;
at least one electrode along at least a portion of the body, the at least one electrode adapted to be electrically connected to a neural stimulator; and
a spacer within the body, the spacer having a first and second end, the first end secured to an inside surface of the body and the second end adapted to pass between the vessel and the nerve and to be secured to the inside surface of the body.

27. The system of claim 26, further comprising:
a third electrode assembly electrically connected to the second electrode assembly along the stabilizer bar, the third electrode assembly including:
a body adapted to at least partially encompass a blood vessel and a nerve proximate to the blood vessel after implantation of the assembly;
at least one electrode along at least a portion of the body, the at least one electrode adapted to be electrically connected to a neural stimulator; and
a spacer within the body, the spacer having a first and second end, the first end secured to an inside surface of the body and the second end adapted to pass between the vessel and the nerve and to be secured to the inside surface of the body.

28. The system of claim 21, wherein the electrode assembly is adapted to deliver selective neural stimulation to the nerve.

29. A method, comprising:
forming an electrode body adapted to encompass a blood vessel and a nerve proximate to the blood vessel, wherein the body is formed to have shape to conform to the blood vessel without restricting blood flow through the vessel;
embedding at least one neural stimulation electrode along at least a portion of the body, the at least one electrode adapted to be electrically connected to a neural stimulator and configured for use to stimulate the nerve; and
forming a spacer within the body, the spacer having a first and second end, the first end secured to an inside surface of the body and the second end adapted to pass between the vessel and the nerve and to be secured to the inside surface of the body.

30. The method of claim 29, further comprising:
forming a fastener adapted to prevent separation from the vessel and nerve after implantation.

31. The method of claim 29, wherein forming the body includes forming the inside surface of the body to conform to the blood vessel and the nerve.

32. The method of claim 29, wherein forming the body includes forming the body with a hollow, cylindrical shape.

33. The method of claim 29, wherein forming the spacer includes forming the spacer with an arc-like shape.

34. The method of claim 29, wherein embedding at least one electrode includes embedding multiple stimulating contacts parallel to one another along the body.

35. The method of claim 29, wherein embedding at least one electrode includes embedding multiple stimulating contacts offset from one another along the body.

36. An electrode assembly, comprising:
an electrode body adapted to encompass a blood vessel and a nerve proximate to the blood vessel, wherein the body has a shape to conform to the blood vessel without restricting blood flow through the vessel;
at least one neural stimulation electrode along at least a portion of the body, the at least one electrode adapted to be electrically connected to a neural stimulator and configured for use to stimulate the nerve; and
a spacer within the body, the spacer having a first and second end, the first end secured to an inside surface of the body and the second end adapted to pass between the vessel and the nerve and to be secured to the inside surface of the body.

37. The electrode assembly of claim 36, wherein the body is adapted to encompass the blood vessel and the nerve proximate to the blood vessel after implantation of the assembly.

38. The electrode assembly of claim 36, wherein the blood vessel has a diameter and the nerve has a diameter, and the diameter of the blood vessel is larger than the diameter of the nerve.

39. A method of using an electrode assembly, comprising:
at least partially encompassing a blood vessel and a nerve proximate to the blood vessel with a body of the assembly, wherein the body includes at least one electrode along at least a portion of the body, the at least one electrode adapted to be electrically connected to a neural stimulator, and wherein the body includes a spacer within the body, the spacer having a first end secured to an inside surface of the body;
passing a second end of the spacer between the vessel and the nerve; and
securing the second end of the spacer to the inside surface of the body.

40. The method of claim 39, further comprising:
delivering selective neural stimulation to the nerve using the neural stimulator and the at least one electrode.

* * * * *

UNITED STATES PATENT AND TRADEMARK OFFICE
CERTIFICATE OF CORRECTION

PATENT NO. : 7,584,004 B2 Page 1 of 1
APPLICATION NO. : 11/151103
DATED : September 1, 2009
INVENTOR(S) : Caparso et al.

It is certified that error appears in the above-identified patent and that said Letters Patent is hereby corrected as shown below:

In column 13, line 5, in Claim 25, delete "eluding" and insert -- eluting --, therefor.

Signed and Sealed this

Fifth Day of January, 2010

David J. Kappos
*Director of the United States Patent and Trademark Office*